United States Patent
Thattaisundaram et al.

(10) Patent No.: US 10,393,671 B2
(45) Date of Patent: Aug. 27, 2019

(54) INTRA-DIE DEFECT DETECTION

(71) Applicant: KLA-Tencor Corporation, Milpitas, CA (US)

(72) Inventors: Govindarajan Thattaisundaram, San Jose, CA (US); Hucheng Lee, Cupertino, CA (US); Lisheng Gao, Morgan Hill, CA (US)

(73) Assignee: KLA-Tencor Corp., Milpitas, CA (US)

( * ) Notice: Subject to any disclaimer, the term of this patent is extended or adjusted under 35 U.S.C. 154(b) by 580 days.

(21) Appl. No.: 15/140,438

(22) Filed: Apr. 27, 2016

(65) Prior Publication Data

US 2016/0321800 A1 Nov. 3, 2016

Related U.S. Application Data

(60) Provisional application No. 62/154,569, filed on Apr. 29, 2015.

(51) Int. Cl.
| | |
|---|---|
| *G01N 21/00* | (2006.01) |
| *G01N 21/95* | (2006.01) |
| *G06T 7/00* | (2017.01) |
| *G01N 21/956* | (2006.01) |
| *G01N 21/88* | (2006.01) |

(52) U.S. Cl.
CPC ... *G01N 21/9501* (2013.01); *G01N 21/95607* (2013.01); *G06T 7/001* (2013.01); *G01N 2021/8883* (2013.01); *G01N 2021/95676* (2013.01); *G01N 2201/0683* (2013.01); *G01N 2201/06113* (2013.01); *G01N 2201/10* (2013.01); *G06T 2207/10056* (2013.01); *G06T 2207/30148* (2013.01)

(58) Field of Classification Search
CPC ..................................................... G01N 21/95
See application file for complete search history.

(56) References Cited

U.S. PATENT DOCUMENTS

| | | | | |
|---|---|---|---|---|
| 5,854,674 A | * | 12/1998 | Lin ........................ | G02B 27/46 356/237.1 |
| 7,570,796 B2 | * | 8/2009 | Zafar ...................... | G03F 1/84 382/144 |

(Continued)

FOREIGN PATENT DOCUMENTS

WO WO-2017185058 A1 * 10/2017 ............. G06T 7/174

*Primary Examiner* — Dave Czekaj
*Assistant Examiner* — Shanika M Brumfield
(74) *Attorney, Agent, or Firm* — Ann Marie Mewherter

(57) ABSTRACT

Methods and systems for detecting defects on a specimen are provided. One system includes one or more computer subsystems configured for acquiring images generated by an imaging subsystem at multiple instances of a pattern of interest (POI) within a die formed on the specimen. The multiple instances include two or more instances that are located at aperiodic locations within the die. The computer subsystem(s) are also configured for generating a POI reference image from two or more of the images generated at the multiple instances of the POI within the die. The computer subsystem(s) are further configured for comparing the images generated at the multiple instances of the POI within the die to the POI reference image and detecting defects in the multiple instances of the POI based on results of the comparing.

22 Claims, 6 Drawing Sheets

(56) References Cited

U.S. PATENT DOCUMENTS

| | | | |
|---|---|---|---|
| 7,676,077 B2* | 3/2010 | Kulkarni | G06F 17/5045 |
| | | | 382/144 |
| 8,126,255 B2* | 2/2012 | Bhaskar | G06T 7/001 |
| | | | 382/141 |
| 8,664,594 B1* | 3/2014 | Jiang | H01J 37/28 |
| | | | 250/306 |
| 8,692,204 B2 | 4/2014 | Kojima et al. | |
| 8,698,093 B1* | 4/2014 | Gubbens | H01J 37/145 |
| | | | 250/396 ML |
| 8,716,662 B1 | 5/2014 | MacDonald et al. | |
| 9,222,895 B2* | 12/2015 | Duffy | G01N 21/9501 |
| 9,846,930 B2* | 12/2017 | Wu | G06T 7/001 |
| 2003/0228050 A1* | 12/2003 | Geshel | G06T 7/0006 |
| | | | 382/149 |
| 2007/0031026 A1* | 2/2007 | Kurihara | G06T 7/001 |
| | | | 382/149 |
| 2013/0271595 A1* | 10/2013 | Hiroi | G01L 315/00 |
| | | | 348/80 |
| 2015/0125065 A1* | 5/2015 | Lee | G06T 5/00 |
| | | | 382/149 |
| 2015/0228063 A1* | 8/2015 | Minakawa | H01J 37/244 |
| | | | 382/151 |
| 2016/0314578 A1 | 4/2016 | Banerjee et al. | |

\* cited by examiner

INTRA-DIE DEFECT DETECTION

BACKGROUND OF THE INVENTION

1. Field of the Invention

The present invention generally relates to methods and systems for intra-die defect detection.

2. Description of the Related Art

The following description and examples are not admitted to be prior art by virtue of their inclusion in this section.

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing (CMP), etch, deposition, and ion implantation. Multiple semiconductor devices may be fabricated in an arrangement on a single semiconductor wafer and then separated into individual semiconductor devices.

Inspection processes are used at various steps during a semiconductor manufacturing process to detect defects on wafers to promote higher yield in the manufacturing process and thus higher profits. Inspection has always been an important part of fabricating semiconductor devices such as ICs. However, as the dimensions of semiconductor devices decrease, inspection becomes even more important to the successful manufacture of acceptable semiconductor devices because smaller defects can cause the devices to fail.

As design rules shrink, however, semiconductor manufacturing processes may be operating closer to the limitations on the performance capability of the processes. In addition, smaller defects can have an impact on the electrical parameters of the device as the design rules shrink, which drives more sensitive inspections. Therefore, as design rules shrink, the population of potentially yield relevant defects detected by inspection grows dramatically, and the population of nuisance defects detected by inspection also increases dramatically. Therefore, more and more defects may be detected on the wafers, and correcting the processes to eliminate all of the defects may be difficult and expensive.

Recently, inspection systems and methods are increasingly being designed to focus on the relationship between defect and design since it is the impact on the design for a wafer that will determine whether and how much a defect matters. For example, some methods have been developed for focusing the inspection on only certain portions of the design printed on the wafer. Those portions of the design may be commonly referred to as "patterns of interest" (POIs).

Currently, POI monitoring may be carried out as an extension of the die-to-die difference strategy employed by current wafer inspection systems for finding defects on semiconductor wafers. In this strategy, outlier detection may be performed by taking the difference between the POI on the so-called reference die and the test die. So long as the defect being searched for does not have a common mode that cancels in the difference between the reference and the test images of the POI, this is a sensible way of performing outlier detection.

There can be, however, a number of disadvantages to the above-described methods for POI-based defect detection. For example, it is impossible to perform outlier detection when common mode defect mechanisms cancel out in the difference between the reference and test images of the POI. In addition, it is impossible to perform intra-die inspections with the current methodology of analyzing differences between adjacent dies, which by definition must involve a plurality of dies.

Accordingly, it would be advantageous to develop systems and methods for intra-die defect detection that do not have one or more of the disadvantages described above.

SUMMARY OF THE INVENTION

The following description of various embodiments is not to be construed in any way as limiting the subject matter of the appended claims.

One embodiment relates to a system configured to detect defects on a specimen. The system includes an imaging subsystem that includes at least an energy source and a detector. The energy source is configured to generate energy that is directed to a specimen. The detector is configured to detect energy from the specimen and to generate images responsive to the detected energy. The system also includes one or more computer subsystems configured for acquiring images generated by the imaging subsystem at multiple instances of a pattern of interest (POI) within a die formed on the specimen. The multiple instances include two or more instances that are located at aperiodic locations within the die. The one or more computer subsystems are also configured for generating a POI reference image from two or more of the images generated at the multiple instances of the POI within the die. The computer subsystem(s) are further configured for comparing the images generated at the multiple instances of the POI within the die to the POI reference image. In addition, the computer subsystem(s) are configured for detecting defects in the multiple instances of the POI based on results of the comparing. The system may be further configured as described herein.

Another embodiment relates to a computer-implemented method for detecting defects on a specimen. The method includes the steps described above. The steps of the method are performed by one or more computer systems. Each of the steps of the method described above may be further performed as described further herein. In addition, the embodiment of the method described above may include any other step(s) of any other method(s) described herein. Furthermore, the method described above may be performed by any of the systems described herein.

Another embodiment relates to a non-transitory computer-readable medium storing program instructions executable on a computer system for performing a computer-implemented method for detecting defects on a specimen. The computer-implemented method includes the steps of the method described above. The computer-readable medium may be further configured as described herein. The steps of the computer-implemented method may be performed as described further herein. In addition, the computer-implemented method for which the program instructions are executable may include any other step(s) of any other method(s) described herein.

BRIEF DESCRIPTION OF THE DRAWINGS

Further advantages of the present invention will become apparent to those skilled in the art with the benefit of the following detailed description of the preferred embodiments and upon reference to the accompanying drawings in which.

Figure 1:
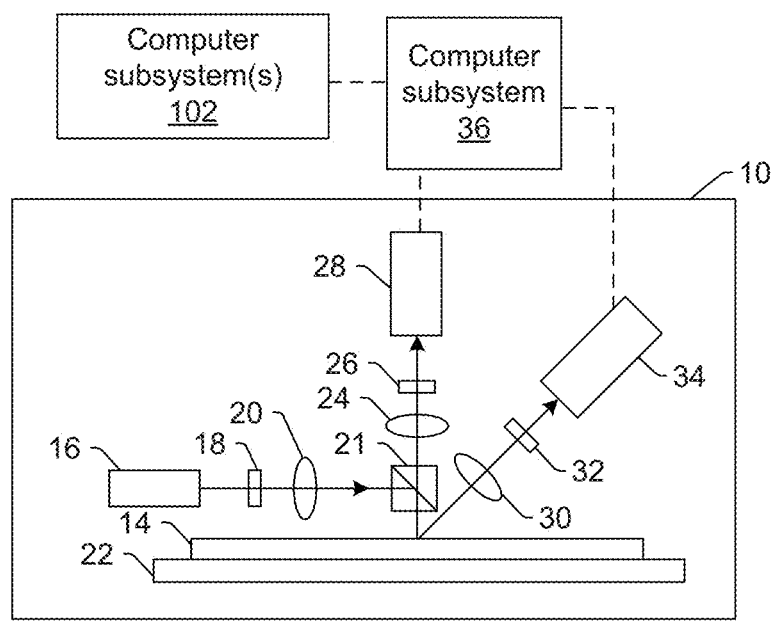
FIGS. 1 and 2 are schematic diagrams illustrating side views of embodiments of a system configured as described herein.

While the invention is susceptible to various modifications and alternative forms, specific embodiments thereof are shown by way of example in the drawings and are herein described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

The terms "design" and "design data" as used herein generally refer to the physical design (layout) of an IC and data derived from the physical design through complex simulation or simple geometric and Boolean operations. The physical design may be stored in a data structure such as a graphical data stream (GDS) file, any other standard machine-readable file, any other suitable file known in the art, and a design database. A GDSII file is one of a class of files used for the representation of design layout data. Other examples of such files include GL1 and OASIS files and proprietary file formats such as RDF data, which is proprietary to KLA-Tencor, Milpitas, Calif. In addition, an image of a reticle acquired by a reticle inspection system and/or derivatives thereof can be used as a "proxy" or "proxies" for the design. Such a reticle image or a derivative thereof can serve as a substitute for the design layout in any embodiments described herein that use a design. The design may include any other design data or design data proxies described in commonly owned U.S. Pat. No. 7,570,796 issued on Aug. 4, 2009 to Zafar et al. and U.S. Pat. No. 7,676,077 issued on Mar. 9, 2010 to Kulkarni et al., both of which are incorporated by reference as if fully set forth herein. In addition, the design data can be standard cell library data, integrated layout data, design data for one or more layers, derivatives of the design data, and full or partial chip design data.

In some instances, simulated or acquired images from a wafer or reticle can be used as a proxy for the design. Image analysis can also be used as a proxy for design analysis. For example, polygons in the design may be extracted from an image of a design printed on a wafer and/or reticle, assuming that the image of the wafer and/or reticle is acquired with sufficient resolution to adequately image the polygons of the design. In addition, the "design" and "design data" described herein refers to information and data that is generated by semiconductor device designers in a design process and is therefore available for use in the embodiments described herein well in advance of printing of the design on any physical wafers.

Preferably, the "design" or "physical design" as those terms are used herein refer to the design as it would be ideally formed on the specimen. For example, a design or physical design described herein would preferably not include features of the design that would not be printed on a wafer such as optical proximity correction (OPC) features, which are added to the design to enhance printing of the features on the wafer without actually being printed themselves. In this manner, in some embodiments, the design for the specimen used for the steps described further herein does not include features of the design that will not be printed on the specimen.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals. Unless otherwise noted herein, any of the elements described and shown may include any suitable commercially available elements.

In general, the embodiments described herein are configured for intra-die defect detection for specimen (e.g., semiconductor wafer) inspection. However, the inspection described herein may also be referred to as within die inspection and in-die inspection. In the embodiments described herein each pattern of interest (POI) is inspected by comparing it to a POI reference image or a "golden" reference POI that is computed from the die in which the POI is located. In other words, a golden POI image is generated for each die and used as a reference to detect defects within the respective dies.

One embodiment relates to a system configured to detect defects on a specimen. In one embodiment, the specimen includes a wafer. In another embodiment, the specimen includes a reticle. The wafer and the reticle may include any wafer and reticle known in the art.

One embodiment of such a system is shown in FIG. 1. The system includes an imaging subsystem that includes at least an energy source and a detector. The energy source is configured to generate energy that is directed to a specimen. The detector is configured to detect energy from the specimen and to generate images responsive to the detected energy.

In one embodiment, the energy directed to the specimen includes light, and the energy detected from the specimen includes light. For example, in the embodiment of the system shown in FIG. 1, imaging subsystem 10 includes an illumination subsystem configured to direct light to specimen 14. The illumination subsystem includes at least one light source. For example, as shown in FIG. 1, the illumination subsystem includes light source 16. In one embodiment, the illumination subsystem is configured to direct the light to the specimen at one or more angles of incidence, which may include one or more oblique angles and/or one or more normal angles. For example, as shown in FIG. 1, light from light source 16 is directed through optical element 18 and then lens 20 to beam splitter 21, which directs the light to specimen 14 at a normal angle of incidence. The angle of incidence may include any suitable angle of incidence, which may vary depending on, for instance, characteristics of the specimen and the defects to be detected on the specimen.

The illumination subsystem may be configured to direct the light to the specimen at different angles of incidence at different times. For example, the imaging subsystem may be configured to alter one or more characteristics of one or more elements of the illumination subsystem such that the light can be directed to the specimen at an angle of incidence that is different than that shown in FIG. 1. In one such example, the imaging subsystem may be configured to move light source 16, optical element 18, and lens 20 such that the light is directed to the specimen at a different angle of incidence.

In some instances, the imaging subsystem may be configured to direct light to the specimen at more than one angle of incidence at the same time. For example, the illumination subsystem may include more than one illumination channel, one of the illumination channels may include light source 16, optical element 18, and lens 20 as shown in FIG. 1 and another of the illumination channels (not shown) may include similar elements, which may be configured differently or the same, or may include at least a light source and possibly one or more other components such as those described further herein. If such light is directed to the specimen at the same time as the other light, one or more characteristics (e.g., wavelength, polarization, etc.) of the light directed to the specimen at different angles of incidence may be different such that light resulting from illumination of the specimen at the different angles of incidence can be discriminated from each other at the detector(s).

In another instance, the illumination subsystem may include only one light source (e.g., source 16 shown in FIG. 1) and light from the light source may be separated into different optical paths (e.g., based on wavelength, polarization, etc.) by one or more optical elements (not shown) of the illumination subsystem. Light in each of the different optical paths may then be directed to the specimen. Multiple illumination channels may be configured to direct light to the specimen at the same time or at different times (e.g., when different illumination channels are used to sequentially illuminate the specimen). In another instance, the same illumination channel may be configured to direct light to the specimen with different characteristics at different times. For example, in some instances, optical element 18 may be configured as a spectral filter and the properties of the spectral filter can be changed in a variety of different ways (e.g., by swapping out the spectral filter) such that different wavelengths of light can be directed to the specimen at different times. The illumination subsystem may have any other suitable configuration known in the art for directing the light having different or the same characteristics to the specimen at different or the same angles of incidence sequentially or simultaneously.

In one embodiment, light source 16 may include a broadband plasma (BBP) light source. In this manner, the light generated by the light source and directed to the specimen may include broadband light. However, the light source may include any other suitable light source such as a laser. The laser may include any suitable laser known in the art and may be configured to generate light at any suitable wavelength or wavelengths known in the art. In addition, the laser may be configured to generate light that is monochromatic or nearly-monochromatic. In this manner, the laser may be a narrowband laser. The light source may also include a polychromatic light source that generates light at multiple discrete wavelengths or wavebands.

Light from optical element 18 may be focused to beam splitter 21 by lens 20. Although lens 20 is shown in FIG. 1 as a single refractive optical element, it is to be understood that, in practice, lens 20 may include a number of refractive and/or reflective optical elements that in combination focus the light from the optical element to the specimen. The illumination subsystem shown in FIG. 1 and described herein may include any other suitable optical elements (not shown). Examples of such optical elements include, but are not limited to, polarizing component(s), spectral filter(s), spatial filter(s), reflective optical element(s), apodizer(s), beam splitter(s), aperture(s), and the like, which may include any such suitable optical elements known in the art. In addition, the system may be configured to alter one or more of the elements of the illumination subsystem based on the type of illumination to be used for imaging.

The imaging subsystem may also include a scanning subsystem configured to cause the light to be scanned over the specimen. For example, the imaging subsystem may include stage 22 on which specimen 14 is disposed during imaging. The scanning subsystem may include any suitable mechanical and/or robotic assembly (that includes stage 22) that can be configured to move the specimen such that the light can be scanned over the specimen. In addition, or alternatively, the imaging subsystem may be configured such that one or more optical elements of the imaging subsystem perform some scanning of the light over the specimen. The light may be scanned over the specimen in any suitable fashion.

The imaging subsystem further includes one or more detection channels. At least one of the one or more detection channels includes a detector configured to detect light from the specimen due to illumination of the specimen by the imaging subsystem and to generate images responsive to the detected light. For example, the imaging subsystem shown in FIG. 1 includes two detection channels, one formed by collector 24, element 26, and detector 28 and another formed by collector 30, element 32, and detector 34. As shown in FIG. 1, the two detection channels are configured to collect and detect light at different angles of collection. In some instances, one detection channel is configured to detect specularly reflected light, and the other detection channel is configured to detect light that is not specularly reflected (e.g., scattered, diffracted, etc.) from the specimen. However, two or more of the detection channels may be configured to detect the same type of light from the specimen (e.g., specularly reflected light). Although FIG. 1 shows an embodiment of the imaging subsystem that includes two detection channels, the imaging subsystem may include a different number of detection channels (e.g., only one detection channel or two or more detection channels). Although each of the collectors are shown in FIG. 1 as single refractive optical elements, it is to be understood that each of the collectors may include one or more refractive optical element(s) and/or one or more reflective optical element(s).

The one or more detection channels may include any suitable detectors known in the art. For example, the detectors may include photo-multiplier tubes (PMTs), charge coupled devices (CCDs), and time delay integration (TDI) cameras. The detectors may also include any other suitable detectors known in the art. The detectors may also include non-imaging detectors or imaging detectors. In this manner, if the detectors are non-imaging detectors, each of the detectors may be configured to detect certain characteristics of the light such as intensity but may not be configured to detect such characteristics as a function of position within the imaging plane. As such, the output that is generated by each of the detectors included in each of the detection channels of the imaging subsystem may be signals or data, but not image signals or image data. In such instances, a computer subsystem such as computer subsystem 36 of the system may be configured to generate images of the specimen from the non-imaging output of the detectors. However, in other instances, the detectors may be configured as imaging detectors that are configured to generate imaging signals or image data. Therefore, the system may be configured to generate the images described herein in a number of ways.

It is noted that FIG. 1 is provided herein to generally illustrate a configuration of an imaging subsystem that may be included in the system embodiments described herein. Obviously, the imaging subsystem configuration described herein may be altered to optimize the performance of the imaging subsystem as is normally performed when designing a commercial inspection system. In addition, the systems described herein may be implemented using an existing imaging subsystem (e.g., by adding functionality described herein to an existing inspection system) such as the 29xx/28xx series of tools that are commercially available from KLA-Tencor, Milpitas, Calif. For some such systems, the methods described herein may be provided as optional functionality of the system (e.g., in addition to other functionality of the system). Alternatively, the system described herein may be designed "from scratch" to provide a completely new system.

Computer subsystem 36 of the system may be coupled to the detectors of the imaging subsystem in any suitable manner (e.g., via one or more transmission media, which may include "wired" and/or "wireless" transmission media) such that the computer subsystem can receive the images generated by the detectors during scanning of the specimen. Computer subsystem 36 may be configured to perform a number of functions using the images generated by the detectors as described herein and any other functions described further herein. This computer subsystem may be further configured as described herein.

This computer subsystem (as well as other computer subsystems described herein) may also be referred to herein as computer system(s). Each of the computer subsystem(s) or system(s) described herein may take various forms, including a personal computer system, image computer, mainframe computer system, workstation, network appliance, Internet appliance, or other device. In general, the term "computer system" may be broadly defined to encompass any device having one or more processors, which executes instructions from a memory medium. The computer subsystem(s) or system(s) may also include any suitable processor known in the art such as a parallel processor. In addition, the computer subsystem(s) or system(s) may include a computer platform with high speed processing and software, either as a standalone or a networked tool.

If the system includes more than one computer subsystem, then the different computer subsystems may be coupled to each other such that images, data, information, instructions, etc. can be sent between the computer subsystems as described further herein. For example, computer subsystem 36 may be coupled to computer subsystem(s) 102 (as shown by the dashed line in FIG. 1) by any suitable transmission media, which may include any suitable wired and/or wireless transmission media known in the art. Two or more of such computer subsystems may also be effectively coupled by a shared computer-readable storage medium (not shown).

Although the imaging subsystem is described above as being an optical or light-based imaging subsystem, the imaging subsystem may be an electron beam-based imaging subsystem. For example, in one embodiment, the energy directed to the specimen includes electrons, and the energy detected from the specimen includes electrons. In this manner, the energy source may be an electron beam source. In one such embodiment shown in FIG. 2, the imaging subsystem includes electron column 122, which is coupled to computer subsystem 124.

Figure 2:
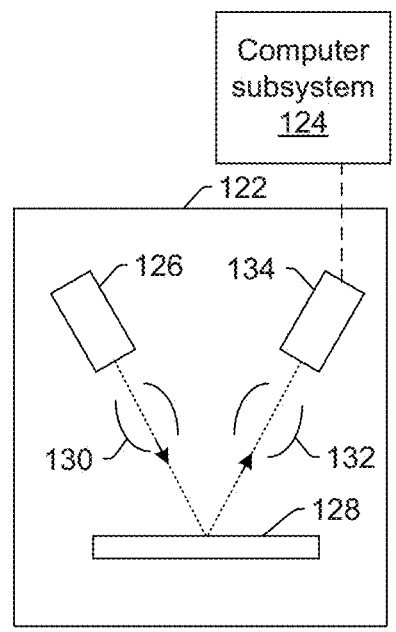

As also shown in FIG. 2, the electron column includes electron beam source 126 configured to generate electrons that are focused to specimen 128 by one or more elements 130. The electron beam source may include, for example, a cathode source or emitter tip, and one or more elements 130 may include, for example, a gun lens, an anode, a beam limiting aperture, a gate valve, a beam current selection aperture, an objective lens, and a scanning subsystem, all of which may include any such suitable elements known in the art.

Electrons returned from the specimen (e.g., secondary electrons) may be focused by one or more elements 132 to detector 134. One or more elements 132 may include, for example, a scanning subsystem, which may be the same scanning subsystem included in element(s) 130.

The electron column may include any other suitable elements known in the art. In addition, the electron column may be further configured as described in U.S. Pat. No. 8,664,594 issued Apr. 4, 2014 to Jiang et al., U.S. Pat. No. 8,692,204 issued Apr. 8, 2014 to Kojima et al., U.S. Pat. No. 8,698,093 issued Apr. 15, 2014 to Gubbens et al., and U.S. Pat. No. 8,716,662 issued May 6, 2014 to MacDonald et al., which are incorporated by reference as if fully set forth herein.

Although the electron column is shown in FIG. 2 as being configured such that the electrons are directed to the specimen at an oblique angle of incidence and are scattered from the specimen at another oblique angle, it is to be understood that the electron beam may be directed to and scattered from the specimen at any suitable angles. In addition, the electron beam-based imaging subsystem may be configured to use multiple modes to generate images of the specimen (e.g., with different illumination angles, collection angles, etc.). The multiple modes of the electron beam-based imaging subsystem may be different in any image generation parameters of the imaging subsystem.

Computer subsystem 124 may be coupled to detector 134 as described above. The detector may detect electrons returned from the surface of the specimen thereby forming electron beam images of the specimen. The electron beam images may include any suitable electron beam images. Computer subsystem 124 may be configured to perform any of the functions described herein using the output of the detector and/or the electron beam images. Computer subsystem 124 may be configured to perform any additional step(s) described herein. A system that includes the imaging subsystem shown in FIG. 2 may be further configured as described herein.

It is noted that FIG. 2 is provided herein to generally illustrate a configuration of an electron beam-based imaging subsystem that may be included in the embodiments described herein. As with the optical imaging subsystem described above, the electron beam-based imaging subsystem configuration described herein may be altered to optimize the performance of the imaging subsystem as is normally performed when designing a commercial inspection system. In addition, the systems described herein may be implemented using an existing inspection system (e.g., by adding functionality described herein to an existing inspection system) such as the eSxxx series of tools that are commercially available from KLA-Tencor. For some such systems, the methods described herein may be provided as optional functionality of the system (e.g., in addition to other functionality of the system). Alternatively, the system described herein may be designed "from scratch" to provide a completely new system.

Although the imaging subsystem is described above as being a light-based or electron beam-based imaging subsystem, the imaging subsystem may be an ion beam-based imaging subsystem. Such an imaging subsystem may be configured as shown in FIG. 2 except that the electron beam source may be replaced with any suitable ion beam source known in the art. In addition, the imaging subsystem may be any other suitable ion beam-based imaging subsystem such as those included in commercially available focused ion beam (FIB) systems, helium ion microscopy (HIM) systems, and secondary ion mass spectroscopy (SIMS) systems.

The one or more computer subsystems included in the system embodiments described herein are configured for acquiring images generated by the imaging subsystem at multiple instances of a POI within a die formed on the specimen. For example, using a recipe, which as described herein may include information for locations of each POI in a die, the imaging subsystem scans the specimen and records images at those locations from one or more (or all) dies on the specimen. In this manner, the imaging subsystem may capture the POI image data at the POI locations determined as described further herein. That image data can then be acquired by the computer subsystem(s) as described further herein. The data that is used by the embodiments described herein may be digital image data, i.e., a two-dimensional (2D) array of numbers on each of its pixels. Each image may be a sample of one particular pattern called the POI on a specimen such as a semiconductor wafer, and all images may have the same dimensions. However, any form of images, images in multiple modes that are aligned to each other, measurements, a vector of measurements, etc. can be used as the images or in place of the images described herein.

Figure 3:
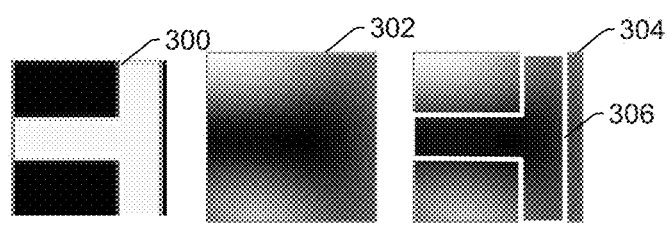
FIG. 3 is a schematic diagram illustrating a plan view of one embodiment of a pattern of interest (POI), an image generated at an instance of the POI formed on a specimen, and the image with information about the design of the POI overlaid thereon.

One specific POI is shown in FIG. 3. Binary image 300 shown in FIG. 3 shows a partial polygon in white, namely a T junction on its side, against a black background. The actual layer of inspection may be a trench layer, i.e., the metal lines that the T represents are still to be filled in with metal. A sample of an optical inspection image of this POI is shown in image 302 in which the trench lines are darker than the surface. Once fine alignment is performed, which may be performed as described further herein, all the samples for this POI may closely resemble image 302 shown in FIG. 3. Overlay of the design polygon edges on the optical image is shown by lines 306 overlaid on image 304.

In one embodiment, the images generated by the imaging subsystem are patch images. For example, the images generated by the imaging subsystem and acquired and used by the computer subsystem(s) may be relatively small images and relatively small portions of all of the image data generated by the imaging subsystem while scanning the specimen. In one such example, a swath of images generated by scanning the specimen may include many frames of image data. Each of the frames may include many patch images. For example, a frame of image data may include hundreds of pixels (e.g., about 512 pixels by 512 pixels) while a patch image may include only tens of pixels (e.g., less than 10 pixels by less than 10 pixels). Therefore, relatively small portions of all of the images generated by scanning the specimen may be used as the images described herein. The patch images generated at the multiple instances of the POI may be extracted from the image data generated by the imaging subsystem in any suitable manner.

Figure 4:
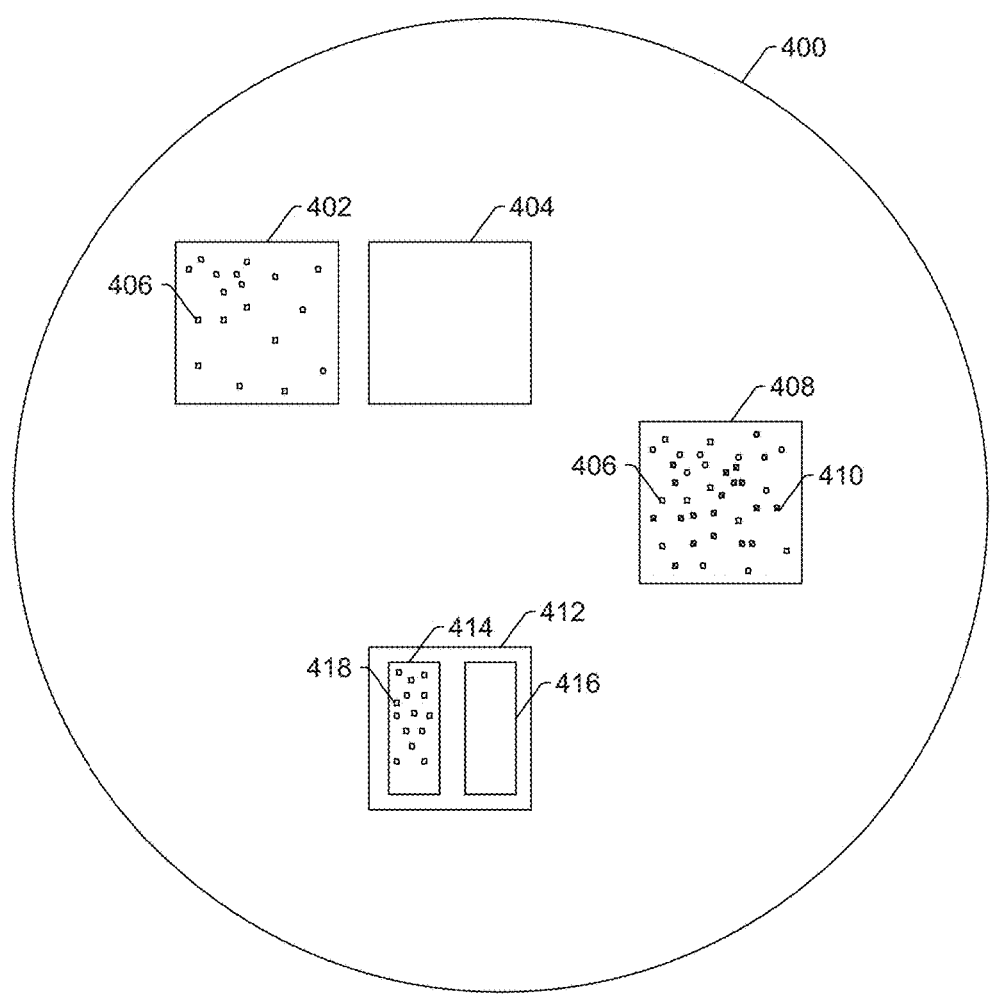
FIG. 4 is a schematic diagram illustrating a plan view of different embodiments of multiple instances of a POI or more than one POI formed within a die or a reticle field on a specimen.

The multiple instances include two or more instances that are located at aperiodic locations within the die. Different embodiments of multiple instances of the POIs are shown in FIG. 4. The specimen is shown in FIG. 4 as wafer 400. Although the embodiments are shown in FIG. 4 with respect to a wafer, the multiple instances may be located as shown in FIG. 4 on other specimens as well. Multiple dies are shown formed on the wafer in a manner that does not necessarily reflect the arrangement of dies on an actual wafer. Instead, the different dies are shown in FIG. 4 simply to illustrate the different locations that the multiple instances of a POI may have within a die.

In one such example, in die 402 shown in FIG. 4, multiple instances 406 of one type of POI are shown. In particular, each of the POIs described herein may be formed in multiple locations or "instances" within a die on the specimen. In addition, there may be different types of POIs within a die on the specimen, and each of the different types may appear at different (one or more) locations within the die. In die 402, multiple instances 406 are for only one type of POI.

As further shown in FIG. 4, multiple instances 406 are not located at periodic locations within die 402. In particular, multiple instances 406 do not appear at regularly spaced intervals along either dimension (e.g., the x or y dimension). In this manner, the multiple instances of the POI are not equivalent to cells in an array region of a die that are formed at periodic locations in both x and y dimensions. In addition, the multiple instances of the POI are not equivalent to fields within a die where each field size is on the order of a few microns and all fields are expected to lie on the same coordinates in one dimension within a die. Instead, the POIs may be much smaller than a field size (e.g., on the order of a single feature or polygon in the die or even only a portion of a single feature or polygon in the die). In particular, while a field size may be on the order of a few microns, a typical POI size may be on the order of only a few nanometers. In addition, the POIs do not necessarily lie along the same coordinates in one dimension in the die. The multiple instances of the POI may be therefore located randomly throughout the die in both dimensions (although the multiple instances of the POI are not necessarily random in that their locations are dictated by the design for the die).

Although the embodiments are described herein with respect to POIs, the embodiments described herein are applicable to hot spot inspection as well, where the sizes of the hot spots are on the order of a few hundred nanometers. A "hot spot" can be generally defined as an area in a design for a device that is known to be more susceptible to defects than other areas in the design. Therefore, "hot spots" are generally more interesting to a user in terms of defect detection or inspection than are other portions of the design. There could be a few hundred types of such POIs and approximately a million locations of each POI type that are scattered across a die.

As further shown in FIG. 4, multiple instances 406 may be located in die 402 but not die 404 on the specimen. In particular, as described further herein, the computer subsystem(s) may perform the steps described further herein (e.g., generating a POI reference image and defect detection) for only a single die on the specimen. Therefore, the multiple instances of a POI that are used for generating a POI reference image and detecting defects may include only the multiple instances of a POI in one die on the specimen (e.g., die 402) and not other dies on the specimen (e.g., not die 404). However, the generation of a POI reference image and defect detection described herein may be performed by the computer subsystem(s) separately for different dies on the specimen (e.g., on a die-by-die basis). In this manner, generation of a POI reference image and defect detection may be performed for die 402 using only multiple instances 406 in die 402, and generation of a POI reference image and defect detection may be performed for die 404 using only multiple instances (not shown) in die 404. If the defect detection (and POI reference image generation) is performed separately for different dies, then the same within die coordinates of multiple instances of a POI may be used for each of the different dies. For example, if POI reference image generation and defect detection is to be performed for die 404 based on the same type of POI formed at multiple instances 406 in die 402, then the same within die locations of the multiple instances may be used for POI reference image generation and defect detection performed for die 404.

As described further herein, POI reference image generation and defect detection may be performed separately for different POIs, and the different POIs may be located in the same die. For example, as shown in die 408 in FIG. 4, POI reference image generation and defect detection may be performed for die 408 and one POI type formed at multiple instances 406. POI reference image generation and defect detection may also be performed for die 408 and a different POI type formed at multiple instances 410. Multiple instances 406 may be arranged within die 408 as described further herein. Multiple instances 410 of the second POI type may be arranged in the same manner within die 408 as described with respect to multiple instances 406 (e.g., at aperiodic locations in one or both dimensions, at seemingly random locations, at locations dictated by the design for the die, etc.). In addition, POI reference image generation and defect detection may be separately performed for any one die any number of times depending on the number of different types of POIs for which the defect detection will be performed. In other words, POI reference image generation and defect detection may be performed separately two or more times for two or more different types of POIs located in the die.

As further described herein, the POI reference image generation and defect detection may be performed on a field basis. For example, as shown in FIG. 4, die 412 may include two different fields 414 and 416 (although a die may include any suitable number of fields located within the die in any suitable arrangement). POI reference image generation and defect detection may be separately performed for each of the fields or only some of the fields. For example, as shown in FIG. 4, POI reference image generation and defect detection may be performed for field 414 and one type of POI located at multiple instances 418 while POI reference image generation and defect detection may not be performed for field 416 (hence, no multiple instances are shown in field 416). POI reference image generation and defect detection may otherwise be performed for the fields as described herein (e.g., on a POI type-by-POI type basis such that for any one field, POI reference image generation and defect detection may be performed separately for different POI types; on a field-by-field basis such that POI reference image generation and defect detection is performed separately for different fields; etc.).

The embodiments described herein are therefore different from currently used methods for defect detection such as die-to-die inspection, field-to-field inspection, and cell-to-cell inspection. For example, die-to-die inspection generally involves comparing images generated for one die on a specimen to images generated for its neighboring die on the specimen. Field-to-field inspection (within a die) involves comparing images generated for one field in a die on a specimen to images generated for a different field within the same die on the specimen. Each field size may be on the order of a few microns, and all fields are expected to lie on the same y-coordinates within the die. Cell-to-cell inspection is applicable to array inspection which has a contiguous repeating pattern with a specific cell size.

The embodiments described herein therefore may not have a number of disadvantages of such currently used methods. For example, die-to-die inspection has an inherent disadvantage of color variation across dies which affects the achievable inspection sensitivity. In particular, since color variation from die-to-die may be detected by die-to-die inspection as defects, the sensitivity of such inspection may have to be set lower than desired in order to not detect the color variation as defects. In addition, field-to-field inspection has a lower limit restriction on the size of the field hence making it not applicable to a hot spot inspection use case. Moreover, all fields are expected to lie on the same y-coordinate within a die. Furthermore, cell-to-cell inspection is applicable to only array regions, which have contiguous repeating patterns.

In an additional embodiment, the computer subsystem(s) are configured for receiving information for the POI and identifying all of the multiple instances of the POI in the die based on the information. For example, before defect detection, one or more steps may be performed on a set of dies (or one or more dies) on a wafer, a complete wafer (i.e., all of the dies on a wafer), or a lot (i.e., one or more dies on one or more wafers in a lot). In one such example, a user may define POI or care areas using design information for the specimen. In this manner, a user may mark POI on the design layout. A plurality of POIs or different types of POIs can be marked. The computer subsystem(s) described herein may receive such information in any suitable manner. The computer subsystem(s) may then use an automated pattern search software tool to find all locations of each POI in the die (or other area for which the defect detection is to be performed). These locations may then be marked in the inspection recipe for the specimen such that during scanning of the specimen, images are acquired at the POI locations. In addition, POI images and their corresponding design clips can be grabbed for all POI locations. The design clips may be grabbed so that they are available for one or more functions such as POI alignment when direct POI alignment of multiple images to each other is not possible. In this manner, the embodiments described herein provide a method by which POIs can be identified automatically, which advantageously takes much less time than the time-consuming manual task of identifying the POIs.

In one embodiment, the one or more computer subsystems include a computer subsystem of an electronic design automation (EDA) tool. For example, for POI identification, the computer subsystem(s) may use EDA physical design analysis tools or apply custom algorithms to the physical design. The EDA tool may include any suitable commercially available EDA tool. In some such embodiments, one or more of the computer subsystems described herein (e.g., computer subsystem(s) 102) may be configured as an EDA tool.

In some embodiments, the computer subsystem(s) are configured for separating all of the identified multiple instances of the POI into a bin, the bin does not include any instances of any different POIs within the die on the specimen, and the computer subsystem(s) are configured for separating the multiple instances in the bin into different sub-bins based on neighboring patterns located adjacent to the POI such that each of the different sub-bins corresponds to a different combination of the POI and one of the neighboring patterns. In this manner, the embodiments described herein may include binning POI images according to the similarity of patterns neighboring (or adjacent, surrounding, etc.) the POI. In other words, the computer subsystem(s) may group POI according to their surrounding geometry. Binning POI patches to split them into subgroups based on interior and peripheral geometry may be performed at run time or during setup or a first pass scan of the specimen.

Figure 3A:
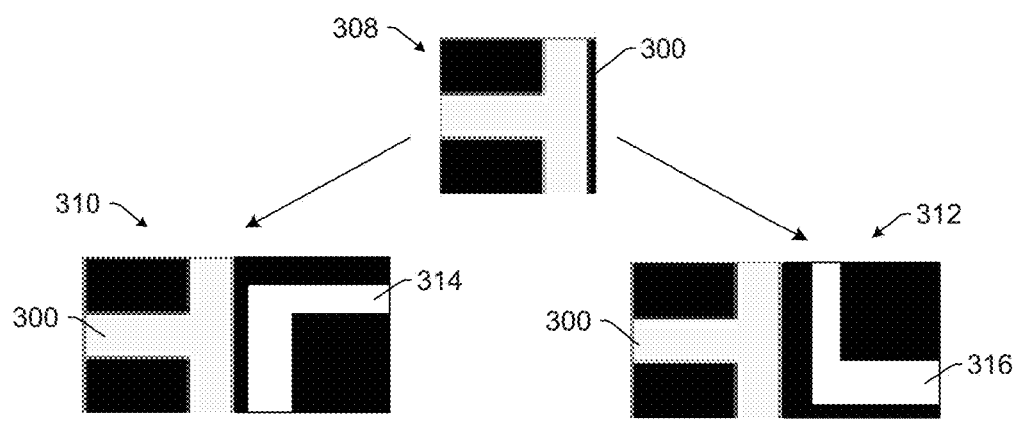
FIG. 3a is a schematic diagram illustrating a plan view of one embodiment of a bin corresponding to a POI and sub-bins corresponding to different combinations of the POI and different neighboring patterns.

In one such embodiment shown in FIG. 3a, binary image 300, which is the same as that shown in FIG. 3, shows a partial polygon in white, namely a T junction on its side, against a black background. That partial polygon may be the POI in this embodiment. In this manner, the partial polygon shown in binary image 300 may be used as the internal geometry of the POI. Therefore, all of the identified instances of the POI may be separated into bin 308, which does not include any other different types of POIs on the specimen. In other words, bin 308 may include only instances of the POI shown in binary image 300.

The multiple instances of the POI in bin 308 may then be separated into different sub-bins based on some peripheral, neighboring, or surrounding geometry. For example, as shown in FIG. 3a, the multiple instances in bin 308 may be separated into sub-bin 310 and sub-bin 312. Each of the sub-bins corresponds to a different combination of the internal geometry and a different peripheral, neighboring, or surrounding geometry. For instance, sub-bin 310 corresponds to the geometry in binary image 300 in combination with the neighboring geometry shown in binary image 314. In contrast, sub-bin 312 corresponds to the geometry in binary image 300 in combination with the neighboring geometry shown in binary image 316. Therefore, each of the different sub-bins contains only instances of one of different combinations of the POI and one of the neighboring patterns. In this manner, the embodiments described herein may have a bin for POI internal geometry with sub-bins below that to separate the POI internal geometry into different groups having different surrounding geometries.

Although the peripheral, neighboring, or surrounding geometry is shown in FIG. 3a as being located on only one side of the internal geometry, the peripheral, neighboring, or surrounding geometry may be defined on one or more sides of the internal geometry. In addition, the external geometry may or may not be located on all sides of the internal geometry. In other words, the external geometry does not necessarily have to surround the POI internal geometry. Furthermore, as shown in FIG. 3a, the different neighboring geometry may be the same geometry with different orientations. However, the different neighboring geometry may be entirely different geometries (e.g., geometries having different numbers of polygons, different shapes of polygons, different sizes of polygons, different orientations of polygons, etc.).

The computer subsystem(s) are also configured for generating a POI reference image from two or more of the images generated at the multiple instances of the POI within the die. In this manner, the embodiments described herein may be configured for computing or generating a "golden" POI image using a set of POI images from each die. In other words, a POI reference image may be generated on a die-by-die basis using only the POI images generated in each die, respectively. In addition, the computer subsystem(s) may generate a golden or reference image for each POI type and for each die in the sample plan. In other words, in the golden POI image computation, a golden-reference image may be computed for each die, for each of the POI types within the die, and binned according to the internal geometry and possibly peripheral geometry of the POI images. In this manner, every die has its own golden reference image for inspection. In addition, every die may have its own golden POI reference image for each POI type. Reference computation may be performed using one or more of the following methods: mean, median, mode, range, and weighted average. In general, any computation method that will minimize differences between the individual POI images (thereby reducing defect information in the POI images) while retaining similarities between the individual POI images (thereby keeping design information in the POI images) to thereby create a substantially defect free POI image can be used to generate the POI reference image.

In one embodiment, generating the POI reference image is performed based on the images generated at all of the multiple instances of the POI within the die. In a different embodiment, generating the POI reference image is performed based on the images generated at fewer than all of the multiple instances of the POI within the die. For example, the computer subsystem(s) can use all of the matching POIs within a given die to generate the POI reference image thereby using the maximum amount of data to generate the POI reference image. Alternatively, the computer subsystem(s) may be configured to pick a selection of the POI images (e.g., that match a constraint in order to be able to contribute towards the golden reference). For example, POI images that are substantially different from other POI images (e.g., due to missing features or due to defects in the POI) may be eliminated from being used in the POI reference image generation. In any case, which and how many of the POI images are used to generate the POI reference image may be determined on a case by case basis to ensure that statistically significant image data is included in the POI reference image generation while possibly eliminating one or more outlier POI images from the calculation.

In one embodiment, the computer subsystem(s) are configured for aligning the two or more of the images generated at the multiple instances of the POI prior to generating the POI reference image. In this manner, the embodiments described herein may be configured for alignment of POI images. In particular, the computer subsystem(s) may be configured to align POI images from a given die and belonging to the same type (based on interior and peripheral geometry) to allow an accurate computation of the golden reference image. Alignment of the POI images may be performed in any suitable manner known in the art.

In an additional embodiment, the computer subsystem(s) are configured for, prior to generating the POI reference image, reducing image artifacts in the acquired images caused by the imaging subsystem or the specimen. As such, the embodiments described herein may be configured for handling and overcoming non-common mode issues such as optical effects, sensor effects, pixel sampling issues, and image alignment. For example, in die-to-die inspection, each pattern may be imaged by the same part of the optics and sensor of the imaging subsystem. Therefore, even if there is any non-uniformity in the optics or sensor, it would not impact die-to-die comparisons because the impact will be canceled out due to the common mode nature of the variations. But for intra-die inspection, since POIs may be scattered across the die, and each POI may be imaged by a different part of the optics and sensor of the imaging subsystem, the impact from non-uniformity of optics and/or sensor would not be canceled out when generating the POI reference image and comparing the POI reference image with each POI image, which may result in higher noise.

In this manner, the computer subsystem(s) may be configured for preprocessing the POI image data acquired at the POI locations identified as described herein. In addition, before any POI reference image generation and defect detection are performed, the image data in the POI may be pre-processed in order to eliminate all (or one or more of) image artifacts generated by the imaging subsystem and/or the specimen. A few of these can be calibrated out. These include but may not be limited to those described further herein.

In one such example, in order to handle non-common mode issues, the images for each POI may undergo one or more of the following effects due to non-uniform optical configuration between the images. The non-common mode optical effects may include, but are not limited to, field dependent aberrations, optical distortion, field uniformity, field tilt, field dependent polarization effects, and illumination incident angle variations across field for non-BF aperture modes. These effects can be handled optically or algorithmically before using the images to generate a POI reference image or using them for intra-die defect detection. In one such example, the image artifacts may include aberration/geometric distortion. For example, a "barrel" or "pin-cushion" distortion of an image or its stretch in a particular direction is often calibrated on an inspection tool. If such a calibration exists, then an inverse geometric transformation can be used to correct for the distortion by re-sampling the image. Generating and using such a calibration may be performed in any suitable manner known in the art.

The non-common mode sensor effects may include, but are not limited to, sensor pixel response across field of view (FOV) and sensor calibration. For example, the image artifacts may include sensor/tap response non-uniformity. In one such example, each tap or pixel of the detector (e.g., a TDI sensor) that records the image on the imaging subsystem may have its own individual gain and offset setting. While it is the responsibility of calibration to make sure that these individual gains and offsets are set such that the response from all of the TDI sensors is the same when presented with the same input, non-uniformity can exist. This non-uniformity may not currently affect defect detection that severely because of the common mode nature of die-to-adjacent die defect detection mechanisms. However, if severe enough, this non-uniformity will affect the defect detection described herein. Therefore, modifying the images to account for such image artifacts can have a significant impact on the defect detection described herein.

In a further example, the image artifacts may include focus drifts in the imaging subsystem. For example, there may be focus drifts on the imaging subsystem that are identified and corrected for on the fly. The focus drifts may be corrected in any suitable manner known in the art. In addition, non-common mode issues due to the stage may include non-common mode thermal effects that may affect patch images alignment, etc.

In yet another example, the image artifacts may include thin film interference effects on the recorded image. For example, thin film interference effects on the specimen can cause color and polarity to change on the recorded image. Algorithmically, one can correct for this effect by adjusting local gain and offsets, which may be performed in any suitable manner known in the art.

The computer subsystem(s) are further configured for comparing the images generated at the multiple instances of the POI within the die to the POI reference image. In this manner, the computer subsystem(s) compare each inspectable POI within each die to the respective golden or reference POI image. In other words, the embodiments described herein perform POI inspection using a golden reference image computed individually for every die. Prior to comparing the images generating at the multiple instances of the POI within the die to the POI reference image, the images being compared may be aligned as described further herein. Comparing the images may be otherwise performed in any manner known in the art. For example, comparing the images may include subtracting the POI reference image from each of the POI images generated at the multiple instances of the POI. In this manner, the results of the comparing may include the differences between the POI images and the POI reference image.

The computer subsystem(s) are also configured for detecting defects in the multiple instances of the POI based on results of the comparing. For example, detecting the defects in the multiple instances of the POI may include applying one or more defect detection methods and/or algorithms to the results of the comparing, which may include any suitable defect detection methods and/or algorithms known in the art. In one embodiment, the results of the comparing include difference images for the multiple instances of the POI, and detecting the defects includes applying a defect detection method to the difference images. For example, subtracting the POI reference image from the POI images as described above may generate difference images (images illustrating the differences between the POI reference image and each of the POI images). A defect detection method and/or algorithm may then be applied to those differences images. In one such example, a threshold of a defect detection method and/or algorithm may be applied to the difference images, any of the difference images having one or more characteristics (e.g., one or more gray levels of one or more pixels) above the threshold may be identified as defects or potential defects while any of the difference images having no characteristics above the threshold may not be identified as defects or potential defects. However, the embodiments described herein are not limited in that any suitable defect detection method and/or algorithm known in the art may be applied to the results of the comparing step described herein.

The computer subsystem(s) may also be configured to generate any suitable inspection results based on results of detecting the defects. For example, the computer subsystem(s) may be configured to report defects on hot spot locations within each POI.

In one embodiment, the one or more computer subsystems are configured for separately performing acquiring the images, generating the POI reference image, comparing the images, and detecting the defects steps for a different POI within the die formed on the specimen. For example, as described further herein, in any one die, there may be more than one type of POI. There may also be one or more instances of each type of POI in a die. In addition, it may be desirable to perform defect detection for more than one type of POI. Therefore, the POI reference image generation and defect detection described herein may be performed separately for different types of POIs. For example, POI reference image generation and defect detection may be performed for a first type of POI using only the images generated at the multiple instances of the first type of POI, POI reference image generation and defect detection may be performed for a second type of POI using only the images generated at the multiple instances of the second type of POI, and so on.

In another embodiment, the computer subsystem(s) are configured for separately performing acquiring the images, generating the POI reference image, comparing the images, and detecting the defects for different combinations of the POI and different neighboring patterns located adjacent to the POI. For example, as described further herein, the instances of the POI may be separated into sub-bins based on one or more neighboring patterns such that the instances of the POI in any one sub-bin are only those instances having the same neighboring patterns. In this manner, each of the steps described herein may be performed separately for the instances of the POI located adjacent to different neighboring patterns. For example, different POI reference images may be generated for different sub-bins of the POI corresponding to different neighboring patterns. In addition, a POI reference image may be compared to only the images generated at the instances of the POI included in the sub-bin for which it was generated. Detecting the defects may also be separately performed for different sub-bins of the POI corresponding to the different neighboring patterns.

The defect detection that is performed for different POI types and/or different POI sub-bins may be the same or different. For example, since the defect detection may be performed separately for different sub-bins of one POI type, the defect detection that is performed for different sub-bins may be performed with one or more different parameters (e.g., different thresholds). The parameter(s) that are used for defect detection performed for different POI types and/or different POI sub-bins may be determined in any suitable manner based on any suitable information for the POI types and/or POI sub-bins (e.g., estimates of noise in the images for the POI types and/or POI sub-bins).

Performing the steps separately for instances of the POI located adjacent to different neighboring patterns may be advantageous since, in some instances, the neighboring patterns located adjacent to the POI can affect the POI images in different ways (e.g., by causing different noise levels in images of the POI). Therefore, creating and using different POI reference images for the POIs located adjacent to different neighboring patterns can provide a POI reference image that is more representative of a defect free image of any one POI (because each POI reference image can more accurately reflect the different contributions of the different neighboring patterns). In addition, using different POI reference images generated separately for the POIs located adjacent to different neighboring patterns can allow the sensitivity of the inspection to be higher than if the same POI reference image is used for defect detection in instances of the POI having different neighboring patterns. In particular, since the POI reference images generated separately for the POIs having different neighboring patterns will be more representative of the defect free images of each of the POI instances, there will be less noise or nuisance in the results of the comparison step, which means that the detection may be performed at a higher sensitivity.

The methodology described herein can be implemented in a variety of ways such as a storage approach and a run-time approach (an in line version).

Figure 5:
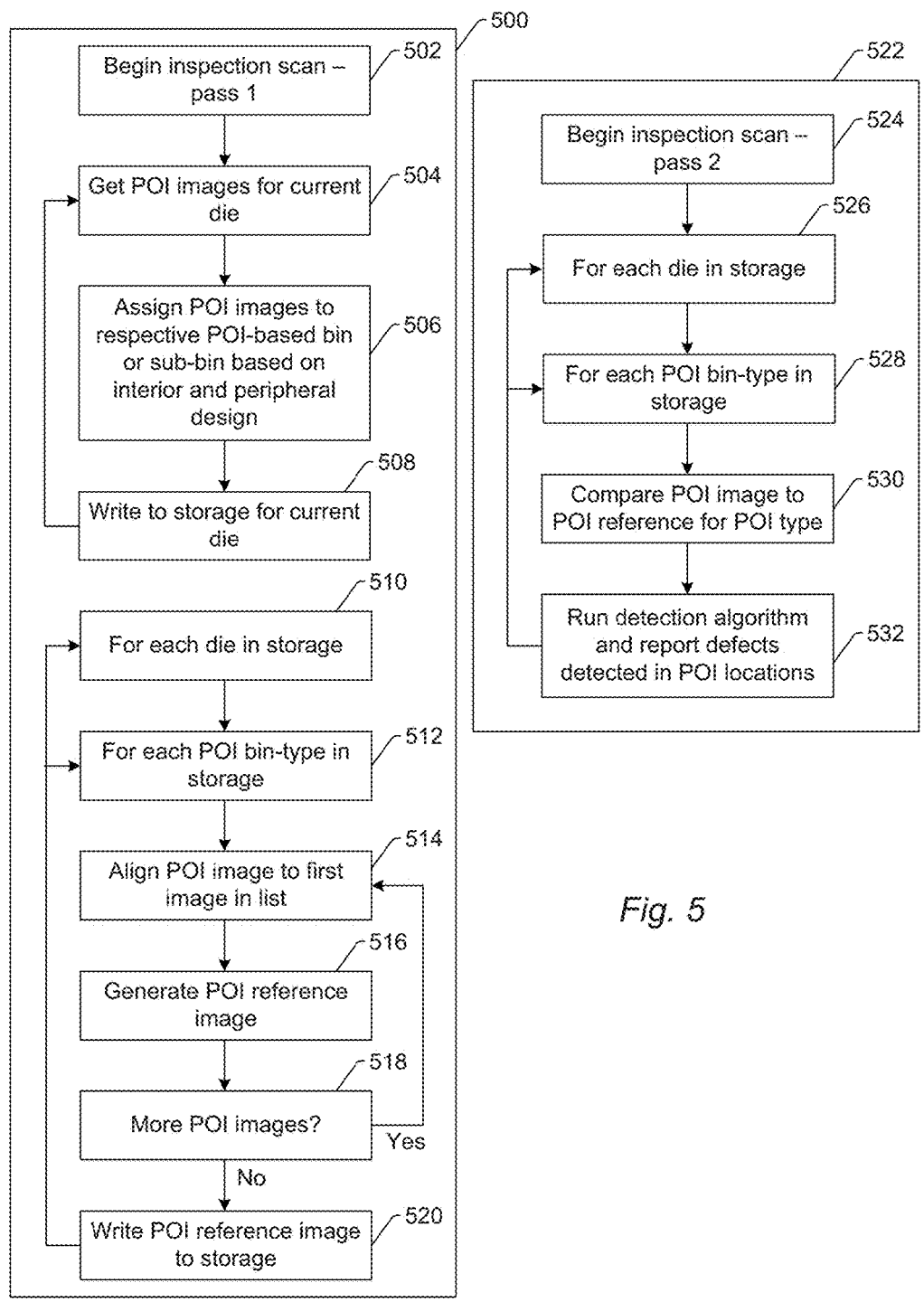
FIGS. 5 and 6 are flow chart illustrating different steps that may be performed by the systems described herein for defect detection.

In some embodiments of a storage approach, the two or more of the images used for generating the POI reference image are generated in a first pass scan of the specimen performed by the imaging subsystem, and the images compared to the POI reference image in the comparing step are generated in a second pass scan of the specimen performed by the imaging subsystem. One such embodiment is shown in FIG. 5. For example, as shown in FIG. 5, portion 500 of the step(s) may be performed by the system in a first pass or a storage portion of the methodology that can be performed for setup of the intra-die inspection. As shown in step 502, the system described herein may begin inspection scan—pass 1. As shown in step 504, in the first inspection scan or pass, the imaging subsystem gets POI images for the current die (i.e., the die being inspected). The POI images may be generated one by one with one or more detectors of the imaging subsystem as described further herein. In addition, as shown in step 506, the computer subsystem(s) may assign POI images to their respective POI-based bin or sub-bin based on interior and peripheral design. The computer subsystem(s) may also be configured for writing the results of step 506 to storage for the current die, as shown in step 508. As further shown in FIG. 5, once step 508 has been performed for one die, steps 504, 506, and 508 may be performed for another die that is to be inspected on the specimen. These steps may be repeated any number of times for any number of dies being inspected on the specimen.

After the images have been generated and stored, the computer subsystem(s) may use the images in storage to generate the POI reference image(s). For example, as shown in step 510, for each die in storage, and as shown in step 512, for each POI bin-type (or sub-bin type) in storage, the computer subsystem(s) may be configured for aligning a POI image to the first image in a list, as shown in step 514. In addition, as shown in step 516, the computer subsystem(s) may be configured for generating a POI reference image. As further shown in step 518, the computer subsystem(s) may be configured for determining if there are more POI images for the die and POI bin type (or sub-bin type). If the computer subsystem(s) determine, in step 518, that there are more POI images for the die and POI bin type (or sub-bin type), the computer subsystem(s) may repeat steps 514 and 516 for the additional POI images. If the computer subsystem(s) determine, in step 518, that there are not any more POI images for the die and POI bin type (or sub-bin type), the computer subsystem(s) may be configured for writing the POI reference image to storage as shown in step 520. After the POI reference image has been generated and stored, the computer subsystem(s) may repeat steps 510, 512, 514, 516, 518, and 520 for any other dies and/or any other POI bin types (or sub-bin types) in the die or the other dies.

As further shown in FIG. 5, portion 522 of the step(s) may be performed by the system in a second pass or a run-time (or in-line) portion of the methodology that can be performed for intra-die inspection. As shown in step 524, the system described herein may begin inspection scan—pass 2. As shown in step 526, for each die in storage, and as shown in step 528, for each POI bin-type (or sub-bin type) in storage, the computer subsystem(s) may be configured for comparing the POI image to the POI reference image for the POI type (or sub-bin type) as shown in step 530. In addition, as shown in step 532, the computer subsystem(s) may be configured for running a detection algorithm on results of step 530 and reporting defects detected in the POI locations. Each of the steps shown in FIG. 5 may be performed as described further herein.

In another embodiment of a storage approach, the computer subsystem(s) include a virtual inspection system, the two or more of the images used for generating the POI reference image are generated in a first pass scan of the specimen performed by the virtual inspection system, and the images compared to the POI reference image in the comparing step are generated in a second pass scan of the specimen performed by the virtual inspection system. For instance, a virtual inspection system is also commonly referred to as a virtual inspector (VI). A VI can be generally defined as a computer system that can store massive amounts of output generated for a specimen by an inspection subsystem such that the output can be "played back" in a manner that mimics real time acquisition of the output during which a virtual inspection can be performed for the specimen using only the stored output. In this manner, a VI can be used to perform the steps shown in FIG. 5 except that both scans shown in FIG. 5 may be performed using the same images generated in the same pass or scan of the specimen and stored in the VI. Therefore, only one actual scan or pass of the specimen may be performed by the imaging subsystem although multiple virtual scans or passes may be performed using the same data generated by that one actual scan or pass. Examples of such virtual inspectors are illustrated in U.S. Pat. No. 8,126,255 issued on Feb. 28, 2012 to Bhaskar et al. and U.S. Pat. No. 9,222,895 issued on Dec. 29, 2015 to Duffy et al., which are incorporated by reference as if fully set forth herein. The computer subsystem(s) described herein may be further configured as described in these patents.

In a further embodiment, the two or more of the images used for generating the POI reference image and the images compared to the POI reference image in the comparing step are generated in the same pass scan of the specimen performed by the imaging subsystem. For example, the system may perform detection within the patch images in storage after a golden POI image is generated. A second pass scan is therefore not performed in these embodiments.

Figure 6:
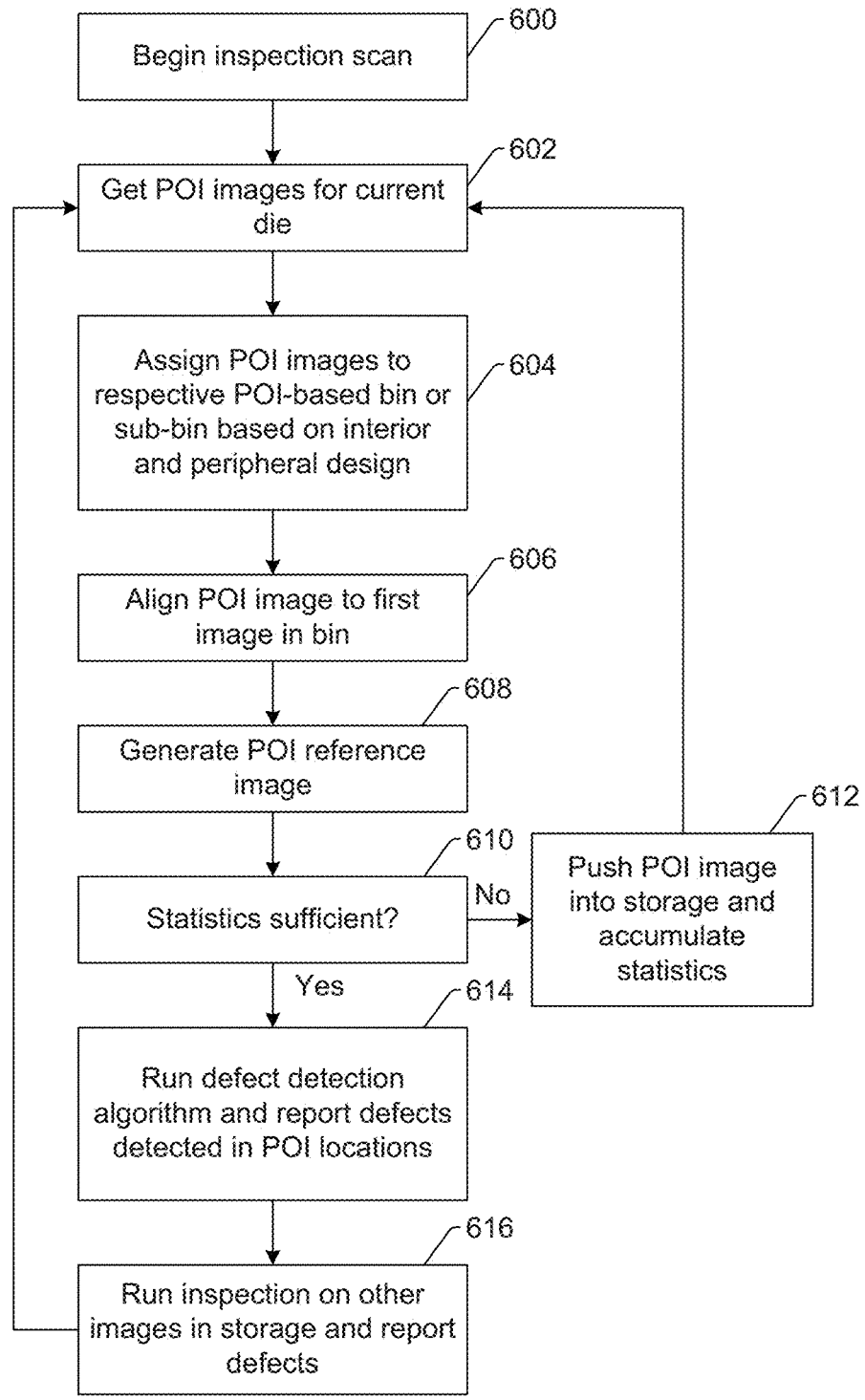

One embodiment of a run-time approach (in line detection) is shown in FIG. 6. In this embodiment, the system may begin the inspection scan as shown in step 600. As shown in step 602, in the inspection scan, the imaging subsystem gets POI images for the current die (i.e., the die being inspected). The POI images may be generated one by one with one or more detectors of the imaging subsystem. In addition, as shown in step 604, the computer subsystem(s) may assign POI images to their respective POI-based bin or sub-bin based on interior and peripheral design. As shown in step 606, the computer subsystem(s) may align the POI image to the first image in a bin. As further shown in step 608, the computer subsystem(s) may generate a POI reference image. As shown in step 610, the computer subsystem(s) may determine if there are sufficient statistics. For example, the computer subsystem(s) may be configured to determine if the POI reference image is generated based on enough data (e.g., a minimum of 3 POI images) to be statistically significant. If the statistics are determined to not be sufficient, the computer subsystem(s) may push the POI image into storage (e.g., stack memory) and accumulate statistics. After the computer subsystem(s) push the POI image into storage, the computer subsystem(s) may repeat steps 602, 604, 606, 608, and 610 for the next instance of a POI in the current die (or if there are no more instances of the POI in the current die, then for the next POI).

If the statistics are determined to be sufficient, the computer subsystem(s) may run a defect detection algorithm and report defects detected in the POI locations, as shown in step 614. The computer subsystem(s) may also run inspection (e.g., perform one or more defect detection algorithms and/or methods) on other images in storage (e.g., in stack memory) and report defects, as shown in step 616. After running inspection on other images in storage, the computer subsystem(s) may repeat the steps beginning at step 602 for any other instances of the POI or any other POIs in the die. Each of the steps shown in FIG. 6 may be performed as described further herein.

In an additional embodiment, the POI reference image is not used for detecting defects in any other die on the specimen or any other die on another specimen. For example, as described further herein, different POI reference images may be generated for different dies on the specimen. In this manner, different POI reference images may be used for detecting defects in different dies on the specimen. In addition, as described further herein, different POI reference images may be generated for different POI types in the same die. Therefore, different POI reference images may be used for detecting defects in different POI types in the same die on the specimen. As such, POI reference image generation and defect detection may be separately performed on a POI type and die basis.

In another embodiment, the die is a single instance of multiple dies formed on the specimen, and the multiple instances for which acquiring the images, generating the POI reference image, comparing the images, and detecting the defects are performed are located only within the single instance of the multiple dies. For instance, the population of POI images may be restricted to be within one die. In such embodiments, therefore, it is inherent that detecting defect in this population is equivalent to performing intra-die inspection. In addition, one of the major applications of the embodiments described herein is for intra-die inspection. In contrast, it is currently impossible to perform intra-die inspections with the current methodology of analyzing differences between adjacent dies, because those methods must by definition involve a plurality of dies. The importance of intra-die inspection is that defects that are not picked up due to the common modes existing between adjacent dies can now be detected. In other words, the defect detection described herein may detect defects that cannot otherwise be detected by currently used die-to-die detection.

The embodiments described herein may, however, be configured to perform the intra-die inspection multiple times for multiple dies on the specimen. For example, the intra-die inspection may be performed for a first die on the specimen then the intra-die inspection may be performed separately for a second die on the specimen, and so on for as many dies on the specimen that are to be inspected. The embodiments described herein may also be configured to perform any other type of inspection in addition to the intra-die inspection described herein. For example, the intra-die inspection can be combined with other types of inspection like array (cell-to-cell) or random mode (die-to-die).

The embodiments described herein have, therefore, a number of advantages over other currently used defect detection methods and systems. For example, the embodiments described herein do not have die-to-die color variation issues that are noticed in current die-to-die inspection algorithms. In addition, the embodiments described herein do not have restrictions of field-to-field inspection such as restricted y coordinates of a field and lower limit restrictions on field size. Furthermore, the embodiments described herein eliminate the need for contiguous repeating patterns as in a cell-to-cell inspection. Intra-die inspection described herein could also potentially lower the noise floor, which can result in increased sensitivity for defect detection.

As an alternative to the embodiments described herein, within each die, every POI can be compared to two previously encountered POIs (in the sequence of inspection) and double detection can be performed for defect detection without computing a golden reference POI patch across the entire die. Such inspection will eliminate the need for two scans, but has the limitation of substantially low image pixels available for computing statistics for defect detection.

In a further embodiment, the die is the only die formed on the specimen. For instance, since the embodiments described herein can perform intra-die inspection, the embodiments may be particularly useful for inspection of specimens that only have a single die formed thereon (e.g., single die reticles).

One can generalize the concept of POI-based defect detection over any subpopulations of POI images. For example, the methods may be die-based as described herein. However, in some embodiments, the multiple instances of the POI are located within only one of multiple reticle fields within the die formed on the specimen. For example, as shown in FIG. 4, multiple instances 418 of a POI are located within only one of multiple reticle fields 414 and 416 in die 412 formed on specimen 400. In other words, although multiple instances may be formed in both of the reticle fields shown in die 412, the multiple instances of the POI that are used for the defect detection described herein may be only those located in one of the reticle fields. For example, the subpopulations can be split into a 2D grid superimposed on each reticle field. In this way, the intra-field deviations in the design pattern can be observed across a reticle field. In this manner, the embodiments described herein can be configured for detecting intra-field deviations across a reticle field.

Another embodiment relates to a computer-implemented method for detecting defects on a specimen. The method includes the steps described above.

Each of the steps of the method may be performed as described further herein. The method may also include any other step(s) that can be performed by the imaging subsystem and/or computer subsystem(s) or system(s) described herein. The steps are performed by one or more computer systems, which may be configured according to any of the embodiments described herein. In addition, the method described above may be performed by any of the system embodiments described herein.

Figure 7:
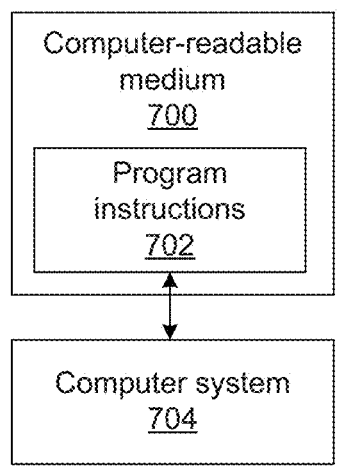
FIG. 7 is a block diagram illustrating one embodiment of a non-transitory computer-readable medium storing program instructions for causing a computer system to perform a computer-implemented method described herein.

An additional embodiment relates to a non-transitory computer-readable medium storing program instructions executable on a computer system for performing a computer-implemented method for detecting defects on a specimen. One such embodiment is shown in FIG. 7. In particular, as shown in FIG. 7, non-transitory computer-readable medium 700 includes program instructions 702 executable on computer system 704. The computer-implemented method may include any step(s) of any method(s) described herein.

Program instructions 702 implementing methods such as those described herein may be stored on computer-readable medium 700. The computer-readable medium may be a storage medium such as a magnetic or optical disk, a magnetic tape, or any other suitable non-transitory computer-readable medium known in the art.

The program instructions may be implemented in any of various ways, including procedure-based techniques, component-based techniques, and/or object-oriented techniques, among others. For example, the program instructions may be implemented using ActiveX controls, C++ objects, Java- Beans, Microsoft Foundation Classes ("MFC"), SSE (Streaming SIMD Extension) or other technologies or methodologies, as desired.

Computer system 704 may be configured according to any of the embodiments described herein.

Further modifications and alternative embodiments of various aspects of the invention will be apparent to those skilled in the art in view of this description. For example, methods and systems for detecting defects on a specimen are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to detect defects on a specimen, comprising:
    an imaging subsystem comprising at least an energy source and a detector, wherein the energy source is configured to generate energy that is directed to a specimen, and wherein the detector is configured to detect energy from the specimen and to generate images responsive to the detected energy; and
    one or more computer subsystems configured for:
        acquiring images generated by the imaging subsystem at multiple instances of a pattern of interest within a die formed on the specimen, wherein the multiple instances comprise two or more instances that are located at aperiodic locations within the die;
        generating a pattern of interest reference image from two or more of the images generated at the multiple instances of the pattern of interest within the die, wherein the one or more computer subsystems pick a selection of the images used for generating the pattern of interest reference image by eliminating any one or more outliers in the images generated at the multiple instances of the pattern of interest within the die from use in generative the pattern of interest reference image;
        comparing the images generated at the multiple instances of the pattern of interest within the die to the pattern of interest reference image; and
        detecting defects in the multiple instances of the pattern of interest based on results of the comparing.

2. The system of claim 1, wherein the one or more computer subsystems are further configured for separately performing said acquiring, said generating, said comparing, and said detecting for a different pattern of interest within the die formed on the specimen.

3. The system of claim 1, wherein the results of the comparing comprise difference images for the multiple instances of the pattern of interest, and wherein said detecting comprises applying a defect detection method to the difference images.

4. The system of claim 1, wherein the one or more computer subsystems are further configured for aligning the two or more of the images generated at the multiple instances of the pattern of interest prior to generating the pattern of interest reference image.

5. The system of claim 1, wherein the one or more computer subsystems are further configured for receiving information for the pattern of interest and identifying all of the multiple instances of the pattern of interest in the die based on the information.

6. The system of claim 5, wherein the one or more computer subsystems are further configured for separating all of the identified multiple instances of the pattern of interest into a bin, wherein the bin does not include any instances of any different patterns of interest within the die on the specimen, and wherein the one or more computer subsystems are further configured for separating the multiple instances in the bin into different sub-bins based on neighboring patterns located adjacent to the pattern of interest such that each of the different sub-bins corresponds to a different combination of the pattern of interest and one of the neighboring patterns.

7. The system of claim 1, wherein the one or more computer subsystems are further configured for separately performing said acquiring, said generating, said comparing, and said detecting for different combinations of the pattern of interest and different neighboring patterns located adjacent to the pattern of interest.

8. The system of claim 1, wherein generating the pattern of interest reference image is performed based on the images generated at fewer than all of the multiple instances of the pattern of interest within the die.

9. The system of claim 1, wherein the one or more computer subsystems are further configured for, prior to said generating, reducing image artifacts in the acquired images caused by the imaging subsystem or the specimen.

10. The system of claim 1, wherein the two or more of the images used for generating the pattern of interest reference image are generated in a first pass scan of the specimen performed by the imaging subsystem, and wherein the images compared to the pattern of interest reference image in said comparing are generated in a second pass scan of the specimen performed by the imaging subsystem.

11. The system of claim 1, wherein the one or more computer subsystems comprise a virtual inspection system, wherein the two or more of the images used for generating the pattern of interest reference image are generated in a first pass scan of the specimen performed by the virtual inspection system, and wherein the images compared to the pattern of interest reference image in said comparing are generated in a second pass scan of the specimen performed by the virtual inspection system.

12. The system of claim 1, wherein the two or more of the images used for generating the pattern of interest reference image and the images compared to the pattern of interest reference image in said comparing are generated in the same pass scan of the specimen performed by the imaging subsystem.

13. The system of claim 1, wherein the pattern of interest reference image is not used for detecting defects in any other die on the specimen or any other die on another specimen.

14. The system of claim 1, wherein the multiple instances of the pattern of interest are located within only one of multiple reticle fields within the die formed on the specimen.

15. The system of claim 1, wherein the die is a single instance of multiple dies formed on the specimen, and wherein the multiple instances for which said acquiring, said generating, said comparing, and said detecting are performed are located only within the single instance of the multiple dies.

16. The system of claim 1, wherein the die is the only die formed on the specimen.

17. The system of claim 1, wherein the specimen comprises a wafer.

18. The system of claim 1, wherein the specimen comprises a reticle.

19. The system of claim 1, wherein the energy directed to the specimen comprises light, and wherein the energy detected from the specimen comprises light.

20. The system of claim 1, wherein the energy directed to the specimen comprises electrons, and wherein the energy detected from the specimen comprises electrons.

21. A non-transitory computer-readable medium, storing program instructions executable on a computer system for performing a computer-implemented method for detecting defects on a specimen, wherein the computer-implemented method comprises:
    acquiring images generated by an imaging subsystem at multiple instances of a pattern of interest within a die formed on a specimen, wherein the multiple instances comprise two or more instances that are located at aperiodic locations within the die, wherein the imaging subsystem comprises at least an energy source and a detector, wherein the energy source is configured to generate energy that is directed to the specimen, and wherein the detector is configured to detect energy from the specimen and to generate images responsive to the detected energy;
    generating a pattern of interest reference image from two or more of the images generated at the multiple instances of the pattern of interest within the die, wherein the method further comprises nicking a selection of the images used for generating the pattern of interest reference image by eliminating any one or more outliers in the images generated at the multiple instances of the pattern of interest within the die from use in generating the pattern of interest reference image;
    comparing the images generated at the multiple instances of the pattern of interest within the die to the pattern of interest reference image; and
    detecting defects in the multiple instances of the pattern of interest based on results of the comparing, wherein said acquiring, said generating, said comparing, and said detecting are performed by the computer system.

22. A computer-implemented method for detecting defects on a specimen, comprising:
    acquiring images generated by an imaging subsystem at multiple instances of a pattern of interest within a die formed on a specimen, wherein the multiple instances comprise two or more instances that are located at aperiodic locations within the die, wherein the imaging subsystem comprises at least an energy source and a detector, wherein the energy source is configured to generate energy that is directed to the specimen, and wherein the detector is configured to detect energy from the specimen and to generate images responsive to the detected energy;
    generating a pattern of interest reference image from two or more of the images generated at the multiple instances of the pattern of interest within the die, wherein the method further comprises nicking a selection of the images used for generating the pattern of interest reference image by eliminating any one or more outliers in the images generated at the multiple instances of the pattern of interest within the die from use in generating the pattern of interest reference image;

comparing the images generated at the multiple instances of the pattern of interest within the die to the pattern of interest reference image; and detecting defects in the multiple instances of the pattern of interest based on results of the comparing, wherein said acquiring, said generating, said comparing, and said detecting are performed by one or more computer systems.

\* \* \* \* \*